United States Patent
Bakker et al.

(10) Patent No.: US 10,603,484 B2
(45) Date of Patent: Mar. 31, 2020

(54) SYSTEM AND METHOD FOR NEUROSTIMULATION AND/OR NEURORECORDING

(71) Applicant: Medtronic Bakken Research Center B.V., Maastricht (NL)

(72) Inventors: Egbertus Johannes Maria Bakker, Wijk en aalburg (NL); Matthew Finlay, Eindhoven (NL); Sébastien Jody Ouchouche, Waalre (NL); Jeroen Jacob Arnold Tol, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 1163 days.

(21) Appl. No.: 14/951,079

(22) Filed: Nov. 24, 2015

(65) Prior Publication Data

US 2016/0144189 A1 May 26, 2016

Related U.S. Application Data

(60) Provisional application No. 62/084,373, filed on Nov. 25, 2014.

(51) Int. Cl.
*A61B 5/0478* (2006.01)
*A61B 5/0476* (2006.01)
(Continued)

(52) U.S. Cl.
CPC ........ *A61N 1/0534* (2013.01); *A61B 5/04001* (2013.01); *A61B 5/0476* (2013.01);
(Continued)

(58) Field of Classification Search
CPC . A61B 5/6868; A61B 5/0478; A61B 5/04001; A61B 5/6877; A61B 5/0476; A61B 2562/04; A61N 1/0534; A61N 1/36185; A61N 1/0476; A61N 1/0529; A61N 1/0531

See application file for complete search history.

(56) References Cited

U.S. PATENT DOCUMENTS

| | | | |
|---|---|---|---|
| 5,999,848 A * | 12/1999 | Gord | A61B 5/14865 607/2 |
| 7,421,297 B2 | 9/2008 | Giftakis et al. | |
| 7,941,202 B2 | 5/2011 | Hetke et al. | |
| 8,588,932 B2 | 11/2013 | Bourget | |

(Continued)

FOREIGN PATENT DOCUMENTS

WO 2010055453 A1 5/2010

*Primary Examiner* — Lee S Cohen
*Assistant Examiner* — Erin M Cardinal
(74) *Attorney, Agent, or Firm* — Shumaker & Sieffert, P.A.

(57) ABSTRACT

The disclosure describes devices and systems that include a grounding electrode. In one example, a system may include a first module including a pulse generator within a first housing, a second module comprising a switch matrix within a second housing distinct from the first housing, a connecting cable that connects the first module to the second module, a grounding electrode disposed distal of the first module and proximal of the second module, and a plurality of electrodes disposed distal of the second module, wherein each electrode of the plurality of electrodes are selectively coupled to the pulse generator via the switch matrix. These devices or system can be used to provide neurostimulation and/or neurorecording.

20 Claims, 9 Drawing Sheets

(51) Int. Cl.
   *A61N 1/05*  (2006.01)
   *A61N 1/36*  (2006.01)
   *A61B 5/00*  (2006.01)
   *A61N 1/04*  (2006.01)
   *A61B 5/04*  (2006.01)

(52) U.S. Cl.
   CPC .......... *A61B 5/0478* (2013.01); *A61B 5/6868* (2013.01); *A61N 1/0476* (2013.01); *A61N 1/0529* (2013.01); *A61N 1/0531* (2013.01); *A61N 1/36185* (2013.01); *A61B 2562/04* (2013.01)

(56) References Cited

U.S. PATENT DOCUMENTS

| | | | |
|---|---|---|---|
| 2001/0025194 A1* | 9/2001 | Ripart | A61N 1/056 607/122 |
| 2002/0169484 A1* | 11/2002 | Mathis | A61N 1/3627 607/9 |
| 2003/0120328 A1* | 6/2003 | Jenkins | A61N 1/0529 607/116 |
| 2003/0139783 A1* | 7/2003 | Kilgore | A61N 1/36003 607/49 |
| 2003/0144719 A1* | 7/2003 | Zeijlemaker | A61N 1/05 607/122 |
| 2003/0149456 A1 | 8/2003 | Rottenberg et al. | |
| 2005/0222658 A1* | 10/2005 | Hoegh | A61N 1/0534 607/116 |
| 2006/0229686 A1* | 10/2006 | Giftakis | A61B 5/6864 607/45 |
| 2007/0100408 A1 | 5/2007 | Gerber | |
| 2009/0270956 A1 | 10/2009 | Vase et al. | |
| 2010/0274115 A1 | 10/2010 | Werder et al. | |
| 2012/0150009 A1 | 6/2012 | Ollivier | |
| 2012/0316620 A1* | 12/2012 | Suaning | A61N 1/37211 607/60 |
| 2013/0116529 A1* | 5/2013 | Min | A61B 5/0006 600/375 |
| 2014/0128937 A1* | 5/2014 | Decre | A61N 1/3606 607/45 |

\* cited by examiner

SYSTEM AND METHOD FOR NEUROSTIMULATION AND/OR NEURORECORDING

This application claims priority to U.S. Provisional Patent Application No. 62/084,373, filed on Nov. 25, 2014 and entitled "A SYSTEM FOR NEUROSTIMULATION AND/OR NEURORECORDING," the entire contents of which are incorporated herein by reference.

TECHNICAL FIELD

The disclosure relates to electrical stimulation and sensing and, more particularly, electrodes for electrical stimulation therapy and sensing.

BACKGROUND

Implantable neurostimulation devices have been used to treat acute or chronic neurological conditions. Deep brain stimulation (DBS), the mild electrical stimulation of subcortical structures, belongs to this category of implantable devices, and has been shown to be therapeutically effective for Parkinson's disease, Dystonia, Essential Tremor, Obsessive Compulsive Disorder, and Epilepsy. New applications of DBS in the domain of psychiatric disorders (clinical depression, anorexia nervosa, schizophrenia) are being researched. In some example systems, a lead carrying four ring electrodes at its tip is connected to an implantable pulse generator to deliver electrical stimulation therapy.

SUMMARY

In general, the disclosure describes techniques, devices, and systems that include a grounding electrode (e.g., a return electrode) for a multi-module system. A system configured to deliver neurostimulation therapy and/or monitor neurosignals may utilize a grounding electrode. The system may include multiple modules distinct from one another, e.g., a first module that includes a pulse generator and/or power supply and a second module that includes a switch matrix for selecting an electrode combination from a plurality of electrodes and a grounding electrode (although other systems may include dedicated current or voltage sources for each electrode such that a switch matrix is not required). The grounding electrode may be located between the first module and the second module. In one example, the grounding electrode may be carried on a connecting cable that transfers power and/or stimulation signals between the first and second modules. In this manner, the system may deliver electrical stimulation signals via one or more electrodes disposed distal of the second module (e.g., disposed on a lead coupled to the second module) and the grounding electrode disposed proximal of the second module.

In one example, the disclosure is directed to a system for neurostimulation that includes a first module comprising a pulse generator within a first housing, a second module comprising a switch matrix within a second housing distinct from the first housing, a connecting cable that connects the first module to the second module, a grounding electrode disposed distal of the first module and proximal of the second module, and a plurality of electrodes disposed distal of the second module, wherein each electrode of the plurality of electrodes are selectively coupled to the pulse generator via the switch matrix.

In another example, the disclosure is directed to a method for neurostimulation that includes generating, by a pulse generator within a first housing of a first module, a stimulation signal, transmitting, by a connecting cable that connects the first module to a second module comprising a switch matrix within a second housing distinct from the first housing, the stimulation signal to at least one electrode of a plurality of electrodes selectively coupled to the pulse generator via the switch matrix, the plurality of electrodes disposed distal of the second module, and returning the stimulation signal to the first module via a grounding electrode disposed distal of the first module and proximal of the second module.

In another example, the disclosure is directed to a method for neurorecording that includes measuring a brain signal between at least one electrode of a plurality of electrodes and a grounding electrode, the grounding electrode disposed distal of a first module comprising a pulse generator within a first housing and proximal of a second module comprising a switch matrix within a second housing distinct from the first housing, the first module and second module being connected by a connecting cable, and the plurality of electrodes disposed distal of the second module, wherein each electrode of the plurality of electrodes are selectively coupled to the pulse generator via the switch matrix.

The details of one or more examples are set forth in the accompanying drawings and the description below. Other features, objects, and advantages of the disclosure will be apparent from the description and drawings, and from the claims.

DETAILED DESCRIPTION

Figure 1:
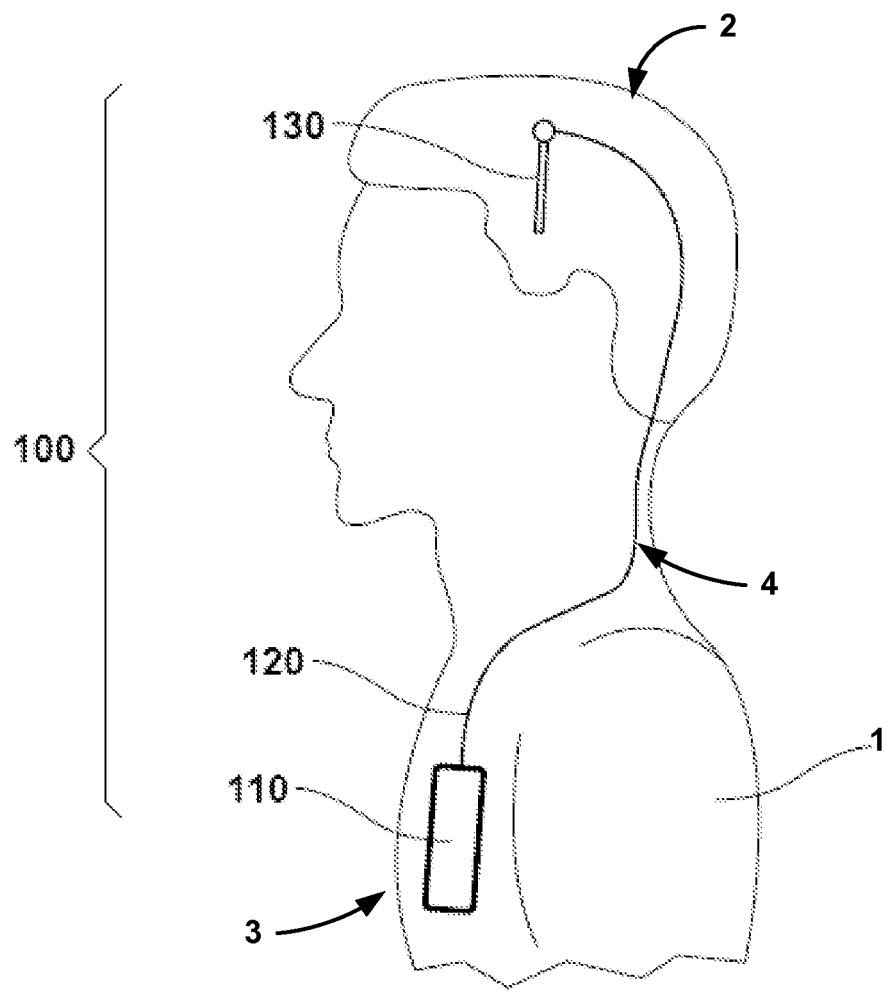
FIG. 1 a conceptual drawing of an example neurostimulation system that delivers deep brain stimulation (DBS) according to the present disclosure.

As described herein, systems, devices, and methods may include a grounding electrode arranged in a system with other electrodes. The grounding electrode may be disposed within the system at a location compatible with components in the system and that facilitates a return path for delivered stimulation signals. For example, the grounding electrode may be carried on a connecting cable between two modules of the system instead of on the same lead that carries a plurality of other electrodes.

Generally, a DBS lead may include a plurality of ring electrodes, e.g., four 1.5 mm-wide cylindrical electrodes at the distal end spaced by 0.5 millimeters (mm) or 1.5 mm. In one example, the diameter of the lead may be 1.27 mm and the metal used for the electrodes and the interconnect wires may be an alloy of platinum and iridium. The coiled interconnect wires coupled to respective electrodes may be insulated individually by a fluoropolymer coating and protected in a urethane tubing having a thickness of a few tens of microns. With this type of electrode and lead design, the electrical current distribution emanates uniformly around the circumference of the cylindrical electrodes, which typically results in stimulation of all areas surrounding the electrode.

Some neurostimulation and/or neurorecording systems may include a greater number of smaller electrodes than traditional systems using a technology based on thin film manufacturing. Examples include a lead made from a thin film based on thin film technology, as e.g., described in WO 2010/055453 A1, and the entire content of WO 2010/055453 A1 is incorporated by reference herein. In some examples, a thin film may carry multiple electrodes to cover the distal tip of the thin film with an array of electrodes, and the thin film may be assembled into a lead. Such leads having an array of electrodes may enhance the precision available to a system to address the appropriate target in the brain and relax the required accuracy of positioning the lead during implantation in the patient. Meanwhile, the electrode array may reduce undesirable side effects due to avoiding undesired stimulation of neighboring areas to target areas. Example leads that are based on thin film manufacturing are, for example, described by U.S. Pat. No. 7,941,202 and have been used in research products in animal studies. The entire content of U.S. Pat. No. 7,941,202 is incorporated by reference herein. However, a ground electrode may not be easily attached to or constructed with a thin film lead.

In some examples, the lack of fine spatial control over current and electric field distributions in cylindrical electrodes results in stimulation that can spread into adjacent structures that are not intended to receive electrical current. To overcome this lack of spatial control, however, systems with high density electrode arrays (e.g., systems with leads constructed of electrodes carried on a thin film) can be used for providing the ability to steer the stimulation field to the appropriate intended target structures instead of unintended structures (hence the term "steering brain stimulation"). The clinical benefit of DBS may be largely dependent on the spatial distribution of the stimulation field in relation to brain anatomy. To improve therapeutic benefits while reducing unwanted side-effects, a DBS system may include stimulation field steering via an electrode array to provide precise control over the stimulation field.

During stimulation with DBS leads, electrodes may be configured to provide monopolar, bipolar, or even multipolar electrical stimulation. Neurostimulator devices with steering brain stimulation capabilities may have a large number of electrode contacts (e.g., an electrode array with more than ten electrodes) that can be connected to electrical circuits such as current sources and/or a system ground. In one example, electrical stimulation may be considered monopolar when the distance between at least one anode and at least one cathode is several times larger than the distance of the cathode to the stimulation target. During monopolar stimulation in homogeneous tissue, the electrical field is distributed roughly spherical similar to the field from a point source. When the anode is located more closely to the cathode, the distribution of the electrical field becomes more directed in the anode-cathode direction. As a result of the closely located anode and cathode, the electrical field may become stronger and neurons are more likely to be activated in this area due to a higher field gradient between the electrodes.

Although the exact mechanisms of DBS are unknown, it is hypothesized that polarization (depolarization and/or hyperpolarization) of neural tissue is likely to play a role both for suppression of clinical symptoms and for induction of stimulation-induced side-effects. In order to activate a neuron it has to be depolarized. In some cases, neurons are depolarized more easily close to the cathode than by the anode (e.g., about 3-7 times more depending on type of neuron or other characteristics in some examples).

Systems configured for neurostimulation and neurorecording may also be subject to noise signals caused by stimulation currents. These noise signals may disturb or otherwise interfere with neurorecording the intrinsic electrical signals from the brain. In some examples, it is an object of the present disclosure to improve a system for neurostimulation and neurorecording, in particular in that the system is capable of reducing the noise signals being caused by the neurostimulation.

As described herein, devices and systems may include a grounding electrode that facilitates neurostimulation and/or neurorecording. For example, a system may include a first module that includes a pulse generator that generates electrical stimulation signals and a second module that includes a switch matrix for switching between different electrodes of the system. A connecting cable may connect the first and second modules, e.g., to transmit power, communication signals, and/or stimulation signals. The grounding electrode may be disposed between the first and second modules, e.g., distal of the first module and proximal of the second module. In addition, a plurality of electrodes may be disposed distal of the second module, e.g., carried by a lead coupled to the second module containing the switch matrix.

In some examples, the connecting cable between the first and second modules may carry the grounding electrode. The grounding electrode may be formed by one or more ring electrodes, ring segment electrodes, coil electrodes, or any combination thereof. The grounding electrode may be disposed on an outside of the connecting cable with exposed edges or embedded within the covering of the connecting cable to create a smooth interface between the grounding electrode and the connecting cable. In some examples, the grounding electrode may have a surface area greater than the combined surface area (i.e., total surface area) of all of the other electrodes disposed on one or more leads coupled to the switch matrix of the second module.

The location of the grounding electrode between two modules may solve one or more complications with certain systems. For instance, in systems including a thin film lead, the thin film lead may not be capable of carrying a grounding electrode because the grounding electrode may not be easily coupled to the thin film. In some examples, placement of the grounding electrode on the second module that houses the switch matrix may result in tissue encapsulation that could compromise the integrity of the switch matrix and/or other electronics within the second module. In addition, adding the grounding electrode (e.g., a cylindrical electrode or conductive housing) to the second module may increase the size and/or volume of the second module.

The second module containing the switch matrix may be configured to be implanted within the skull or at least partially external to the skull of the patient and coupled to the lead implanted within the brain. Therefore, disposing the grounding electrode proximal of the second module and in close proximity to the second module may provide a return path for stimulation signals that facilitates monopolar stimulation, for example, without requiring the stimulation signal to travel relatively long distances (e.g., to an electrode carried by the first module containing the pulse generator and located in the chest of the patient). Furthermore, in contrast to a returning electrode disposed on a housing of the first module, a ground electrode disposed near the switch matrix in the second module may provide a lower resistance path within the system that improves the signal-to-noise ratio when recording intrinsic neuro signals from the patient.

FIG. 1 a conceptual drawing of an example neurostimulation system 100 that delivers deep brain stimulation (DBS) according to the present disclosure. In other examples, neurostimulation system 100 may be directed to other applications such as spinal cord stimulation or pelvic floor stimulation. Neurostimulation system 100 comprises at least a controller 110 (e.g., a first module comprising one or more pulse generators) that may be surgically implanted in the chest region 3 of a patient 1, typically below the clavicle or in the abdominal region of a patient 1. Controller 110 can be configured to supply the necessary stimulation pulses, e.g., in the form of current or voltage pulses (e.g., also referred to as a stimulation signal) to lead arrangement 130. DBS system 100 may further include a connecting cable 120 (e.g., an extension wire) connected to the controller 110 and running subcutaneously to the skull 2, such as along the neck 4, where it terminates in a connector.

DBS lead arrangement 130 may be implanted in the brain tissue, e.g., through a burr-hole in the skull. DBS lead arrangement 130 may include one or more leads coupled to at least one module including a switch matrix. In addition, DBS system 100 may include one or more grounding electrodes. The grounding electrodes may be carried by connecting cable 120, for example, between controller 110 and lead arrangement 130. In some examples, connecting cable 120 may be formed by two or more cables configured to connect to each other, and one or more of these cables may carry a grounding electrode.

Generally, the grounding electrode may be disposed closer to lead arrangement 130 than controller 110. For example, the grounding electrode may be configured to be implanted at least partially outside of skull 2 of patient 1. A plurality of electrodes disposed on a lead of lead arrangement 130 may be configured to be implanted at least partially within brain tissue.

Figure 2A:
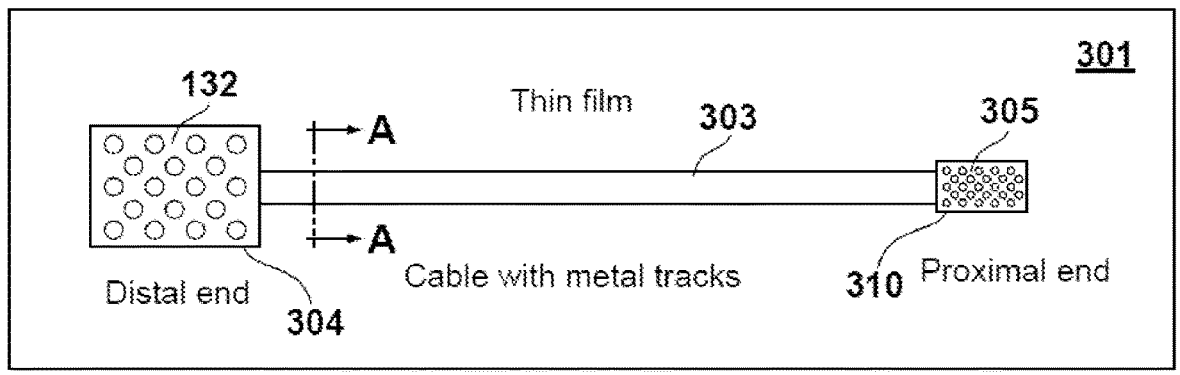
FIGS. 2A, 2B, and 2C are schematic diagrams of an example thin film, lead, and probe of a neurostimulation system for DBS.
Figure 2B:
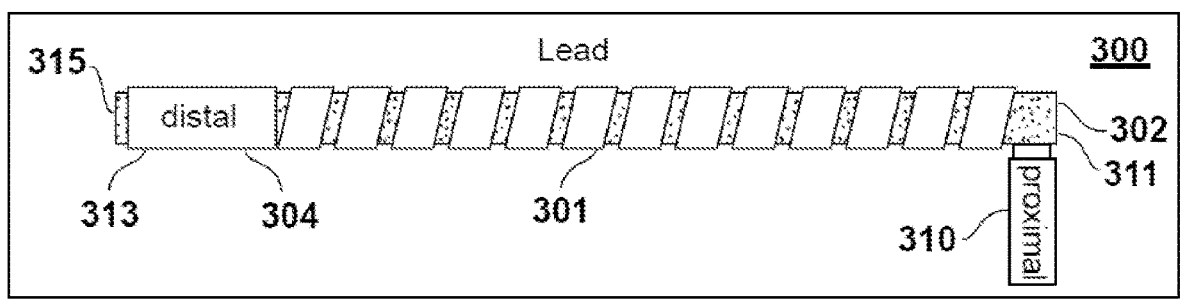
Figure 2C:
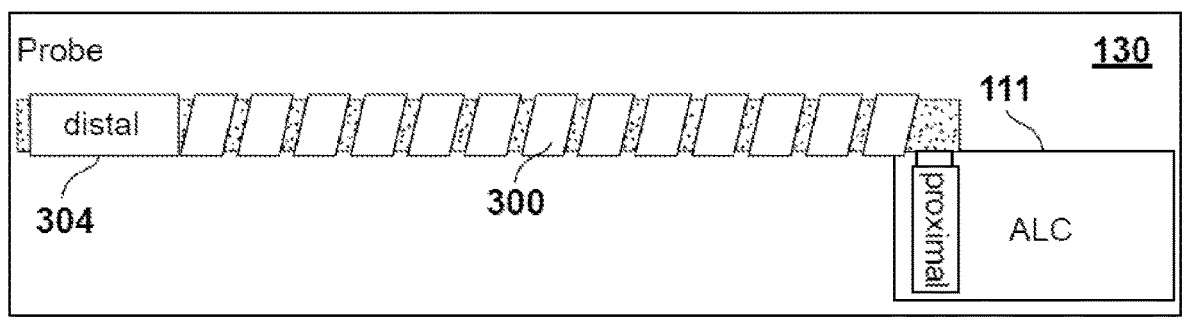

FIGS. 2A, 2B, and 2C are schematic diagrams of an example thin film, lead, and probe of a neurostimulation system for DBS. For example, FIG. 2A illustrates an example, thin film 301, FIG. 2B illustrates an example DBS lead 300, and FIG. 2C illustrates an example Deep Brain Stimulation (DBS) probe 130 that include DBS lead 300 and a second module 111 (e.g., an active lead can (ALC)). Second module 111 may include electronic means to address electrodes 132 disposed on the distal end 304 of the thin film 301. Electrodes 132 may be arranged at the distal end 313 of lead 300 and next to the distal tip 315 of the DBS lead 300.

Lead 300 may include a carrier 302 for thin film 301. Carrier 302 may be sized and shaped to providing the mechanical configuration of DBS lead 300 and the thin film 301. In other words, thin film 301 may be wrapped around the circumference or diameter of carrier 302. Thin film 301 may include at least one electrically conductive layer and may be constructed of a biocompatible material. The thin film 301 may be assembled to carrier 302 and further processed to constitute lead 300.

The thin film 301 for a lead may be formed by a thin film product having a distal end 304, a cable 303 with metal tracks, and a proximal end 310. Proximal end 310 of the thin film 301 may be arranged at the proximal end 311 of lead 300 and is electrically connected to the second module 111. The second module 111 may include the switch matrix of the DBS steering electronics that selects configurations of electrodes 132. The distal end 304 comprises electrodes 132 for brain stimulation, for example. Proximal end 310 of thin film 301 includes interconnect contacts 305 for each metal track in the cable 303. The cable 303 comprises metal tracks or lines (not shown) to electrically connect each of distal electrodes 132 to a respective and designated proximal interconnect contact 305.

Figure 3:
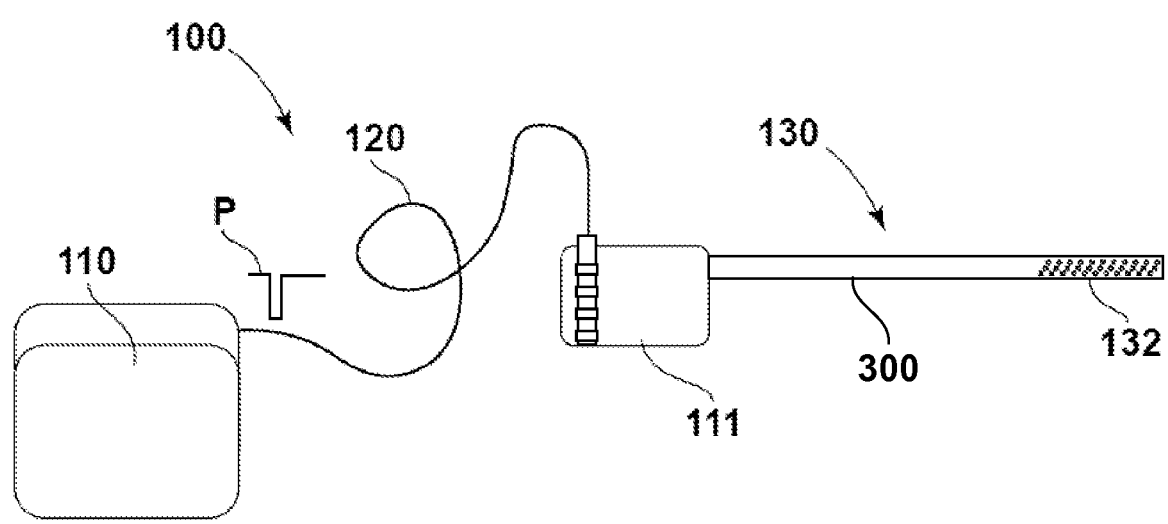
FIG. 3 is a conceptual drawing of an example system that delivers DBS.

Second module 111 may include a switch matrix, or multiplexer, that is used to couple, or decouple, each electrode of electrodes 132 to one or more pulse generator lines and ground provided to second module 111 via a connecting cable (e.g., connecting cable 120 of FIG. 1 or 3). Second module 111 may also be electrically coupled to one or more ground electrodes (e.g., ground electrodes 320A or 320B of FIG. 4). In some examples, second module 111 may include other control electronics, such as a microprocessor or other integrated circuitry, resistors, and capacitors. In still other examples, second module 111 may include one or more signal generators (e.g., one or more pulse generators) that are provided in addition to, or instead of, one or more of the pulse generators provided by controller 110.

FIG. 3 is a conceptual drawing of an example system 100 that delivers DBS. System 100 is described for brain applications, such as neurostimulation and/or neurorecording as a deep brain stimulation system 100 as shown in FIG. 1. The probe system 100 may include at least one probe 130 for brain applications with stimulation and/or recording electrodes 132. In one example, forty electrodes 132 can be provided on the outer body surface at the distal end of the probe 130. Controller 110 (e.g., a first module) may include one or more pulse generators that generate and supply neurostimulation pulses P to a second module 111 (e.g., an active lead can) by means of the connecting cable 120. A switch matrix of the second module 111 may direct the neurostimulation pulses P to the appropriate one or more electrodes for delivery to a patient. In some examples, controller 110 can be or include an implantable pulse generator. In other examples, controller 110 may be configured to simultaneously couple to two or more different second modules 111 and respective probes 130 via one or more connecting cables 120.

As described herein, system 100 may include first module 110 that includes one or more pulse generators. First module 110 may also include components such as a power supply, one or more processors, a memory, a communication unit for transmitting and/or receiving information from an external device, and other components. Second module 111 may include a switch matrix and, in some examples, one or more processors, a memory, and connectors for coupling lead 300 of FIG. 2 (where probe 130 may include second module 111 and lead 300 carrying electrodes 132) and connecting cable 120. Second module 111 may have a housing encompassing the control electronics such as the switch matrix. In some examples, the housing may be electrically nonconductive such as an epoxy or polymer that insulates and protects the components of second module 111. The electrically nonconductive material may reduce encapsulation of the housing and/or insulate the brain from any interference caused by the components of second module 111.

Connecting cable 120 may connect first module 110 to second module 111. The plurality of electrodes 132 are disposed distal of second module 111 and on lead 300 of probe 130. A grounding electrode (not shown in FIG. 3) may be disposed distal of the first module 110 and proximal of the second module 111. In some examples, the grounding electrode is carried by (e.g., formed on, attached to, or otherwise supported by) the connecting cable 120. The grounding electrode may be configured to establish a defined return path for stimulation current from one or more electrodes of the plurality of electrodes (e.g., during monopolar stimulation and/or recording).

The control electronics for the plurality of electrodes 132 and the grounding electrode may provide at least one of neurostimulation and/or neurorecording via at least one electrode of the plurality of electrodes 132 and the grounding electrode. The control electronics are arranged in at least the first module 110 and the second module 111, but one or more additional modules may also include at least some of the control electronics. As described in FIG. 2A, probe 130 may include lead 300 constructed of a thin film 301 carrying the plurality of electrodes 132. Lead 300 may be electrically coupled to the switch matrix of second module 111.

Figure 4:
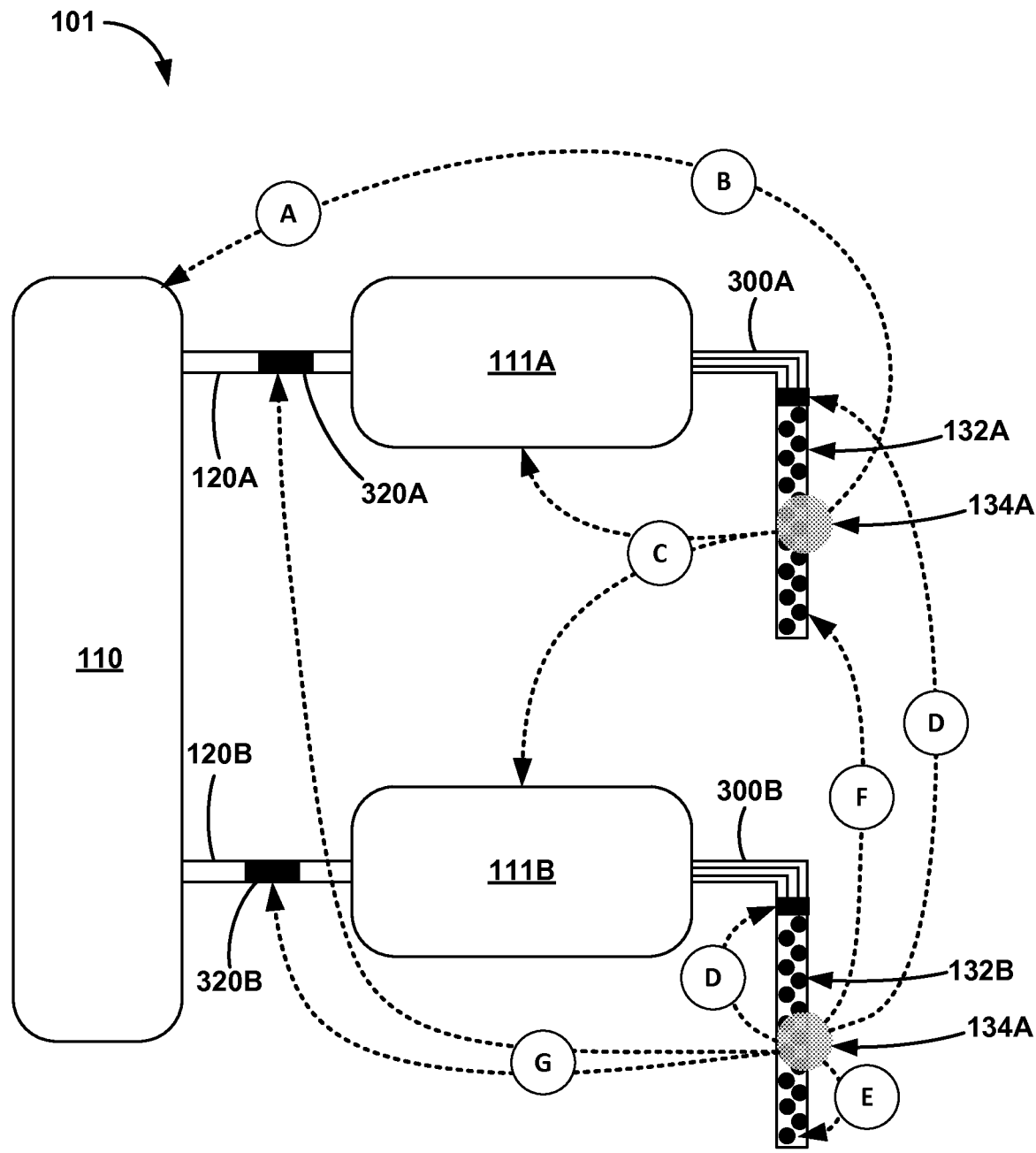
FIG. 4 is a schematic diagram of example return paths for an electrical signal.

FIG. 4 is a schematic diagram of example return paths for an electrical signal using an example system 101. System 101 may be similar to DBS system 100 of FIGS. 1 and 3. However, system 101 includes two modules 111A and 111B coupled to a single module 110 that may include one or more pulse generators. As shown in FIG. 4, there are numerous grounding possibilities in a system for neurostimulation and/or neurorecording, such as a system 101 with a grounding electrode (e.g., grounding electrodes 320A and 320B).

System 101 is shown as including one IPG 110 (e.g., a first module) and two active lead cans 111 (e.g., two second modules), one (module 111A) for the left hemisphere of the brain and one (module 111B) for the right hemisphere of the brain. IPG 110 is shown as a part of system 100 in FIGS. 1 and 3 and also as part of system 101 in FIG. 4. Each module 111A and 111B (collectively "modules 111") is connected to a respective lead 300A and lead 300B (similar to lead 300 of FIGS. 2B and 2C) as described above. All of the return paths A-G are described from a stimulation signal 134A or 134B delivered to the patient from one or more electrodes of respective electrode groups 132A or 132B and returning to respective locations of a grounding electrode. In this manner, a grounding electrode may be provided for delivery of electrical stimulation pulses from the pulse generator within single module 110. Grounding electrodes 320A and 320B are shown on respective connecting cables 120A and 120B to generally illustrate example locations of grounding electrodes described herein. Electrodes 320A and 320B may be electrically connected to the same ground line. In some examples, electrodes 320A and 320B may be coupled to ground via the ground in each respective modules 111A and 111B or to a ground line via connecting cables 120A and 120B connected to module 110.

Return path A corresponds to the placement of a grounding electrode at the chest of the patient, such as on or including the casing (e.g., housing) of IPG 110, and return path B corresponds to placement of the grounding electrode at or including an IPG 110 casing if located at the cranium of the patient. In other words, return paths A and B correspond to return paths to the casing of IPG 110, regardless of whether IPG 110 is implanted in the chest (return path A), the cranium (return path B), or another anatomical location in the patient. However, these locations of a grounding electrode (e.g., a return electrode) may result in increased electrical noise due to the current passing through numerous additional anatomical structures (e.g., nerves, muscles, etc.) as opposed to closer locations for the return path from electrodes 132A and stimulation signal 134A. In addition, the return paths A and B may include greater system resistances because the signal must travel through longer circuit paths or through one or more capacitors and/or resistors in the system. These increased resistances for a return electrode carried by the housing of IPG 110 may require increased power consumption for delivering stimulation signals to the patient.

Return path C corresponds to the placement of a grounding electrode on or including the casing of modules 111 (e.g., the ALC). However, a grounding electrode on the second modules 111 may result in tissue encapsulation around the housing of modules 111 that may compromise the integrity of the housing and/or electrical components therein. Modules 111 may include a housing constructed of an epoxy or insulative polymer, so the housing may not be appropriate for carrying a grounding electrode. In addition, adding a grounding electrode to modules 111 may increase one or more dimensions and/or volume of modules 111 which may be undesirable when modules 111 are configured to be implanted external of the skull and under the skin and/or at least partially within a recess in the scalp or the burr hole.

Return path D corresponds to the placement of a grounding electrode as a dedicated ground contact at or on leads 300A or 300B. However, this location of the grounding electrode for return path D may be too close for some monopolar stimulation (e.g., particularly to electrodes of electrodes 132A and 132B proximal to the grounding electrode). In addition, construction of a grounding electrode on the thin film 301 of the respective leads 300A and 300B may be difficult and/or the grounding electrode may compromise the integrity of the thin film.

Return path E corresponds to using an electrode (e.g., one or several lead contacts at the lead 300B) of one of the plurality of electrodes 132B as the grounding electrode. In this manner. However, the return path E may be relatively short in distance and create a large electrical field gradient not intended for monopolar stimulation. In addition, the surface area of one of electrodes 132B is smaller for use as a ground electrode, which results in a larger electrical field concentration at the grounding electrode. In other words, neurons adjacent to the grounding electrode may be activated due to the close distance between the anode and cathode and/or the relatively small surface area of the grounding electrode.

Return path F corresponds to using an electrode of electrodes 132A on lead 300A as the ground electrode for stimulation signal 134A delivered by one of electrodes 132B on lead 300B. In other words, the return path F leads from one lead to another lead. This configuration for a return path may still be relatively close in distance and the return electrode may have a relatively small surface area, as described with respect to return path E above. In addition, using one of the electrodes of another lead (e.g., one of electrodes 132A) may prevent monopolar stimulation from simultaneously being delivered by lead 300B and lead 300A. In other words, stimulation signal 134A generated by an electrode of electrodes 132A may sink to the grounding electrode of return path F. This may effectively create a large electrical gradient between the electrodes of lead 300A that causes activation of neurons adjacent to the grounding electrode of electrodes 132A.

As an alternative to the above grounding electrode placements, return path G corresponds to the placement of grounding electrodes 320A and 320B (or a single grounding electrode 320 for a single second module 111 and connecting cable 120) on respective connecting cable 120A and 120B. Placement of grounding electrodes 320A and 320B on respective connecting cables 120A and 120B may provide for a sufficient distance for the return path of the electrical stimulation signal that focuses neuron activation around the one or more electrodes delivering stimulation signals 134A and 134B. In addition, grounding electrodes 320A and 320B (collectively "grounding electrodes 320") may reduce internal system resistance and reduce the necessary power to drive stimulation through return path G as opposed to return paths A or B. The above example return paths may be used alone or in combination. In some examples, the grounding electrodes 320 may be disposed closer to the respective second module 111 than the first module 110.

In general the system 101 (and system 100) according to the present disclosure is described in connection with return path G. The system 100 (similar to system 101) is specified in detail above, particularly in connection with FIGS. 1 to 3. The system 101 comprises a plurality of electrodes 132A and 132B on the respective leads 300A and 300B. The control electronics of the system 101 is provided in three modules, i.e., by the IPG 110 and modules 111A and 111B. Note that module 111A may include the same portion of control electronics as module 111B (e.g., module 111A may be identical or substantially similar to module 111B). In some examples, as shown in FIG. 3, system 101 may instead only include a single module 111A coupled to respective lead 300A and connecting cable 120A. Grounding electrode 320 is carried by connecting cable 120A.

Furthermore, the system 101 comprises two grounding electrode 320A and 320B, one grounding electrode for each set of electrodes 132A and 132B. Examples of grounding electrodes 320A and 320B are described in FIGS. 4 to 13. Generally, grounding electrodes 320 are arranged in the vicinity of the control electronics of modules 111, here in the vicinity and adjacent to the respective modules 111.

Example grounding electrodes 320 as shown above create an electrically conducting surface externally to the respective connecting cable 120A and 120B. Grounding electrodes 320 may be electrically coupled to the respective modules 111 while offering as much flexibility as possible. Grounding electrode 320 may include one or more rings, one or more ring segments clipping on the elongated body of a connecting cable 120, a laser cut tube, a thin film carried electrode, a coil or wire, or any other electrically conductive component or components that may function as a grounding electrode for system 101.

The grounding electrodes 320 may use wires, running straight or coiled along the elongated body of the respective connecting cable 120, being internal or external to the elongated body. In some examples, grounding electrodes 320 may be coated and/or opened up for galvanic contact with bodily fluids and/or tissues by subsequent processing (e.g., laser ablation of at least a portion of a coating or housing covering the grounding electrodes). In some examples, conductive coils of the grounding electrodes may be backfilled with adhesive. In other examples, the connection for the grounding electrode can be part of a mounting member, with which connecting cable 120 is mounted to a connector or a can covering the electronics of module 111. The grounding electrodes 320 may be electrically coupled to the switch matrix of the respective second module 111. Each switch matrix may be configured to select an electrode configuration from the plurality of electrodes 132A or 132B and the respective grounding electrode 320.

In some examples, a grounding electrode 320 may be a laser cut-out or a laser ablated electrode. These cut-outs or features of the grounding electrode may provide some mechanical flexibility or an additional transition region as the grounding electrode approaches module 111. In some examples, the connection for the grounding electrodes 320 can join to a neck extending from the respective module 111 or to a tube extending from a mounting member of the respective module 111 to connecting cable 120 of which either could be made flexible by laser-cutting or equivalent processing.

In another example, the grounding electrode can be arranged such that a conductive wire serves as at least a portion of the grounding electrode. The conductive wire may be embedded in a lumen of the elongated body of connecting cable 120 and contacts the surrounding fluid through access holes formed in the elongated body wall of the connecting cable.

Generally, grounding electrodes 320 can be arranged between the implantable pulse generator (IPG) 110 and the modules 111, especially proximal of the modules 111, as shown in FIG. 4 as return path G. In some examples, one or more grounding electrodes described herein can be arranged distal of the modules 111 (e.g., return path D). In any example, the grounding electrodes may be disposed in the vicinity of the modules 111.

The grounding electrodes 320 may be, in the implanted state of the system 101, only partially covered, or not covered, by the tissue to be stimulated. The tissue can be at least partially brain tissue. Additionally or alternatively, the grounding electrode 320 may be at least partially placed in the vicinity of the and/or at least partially outside of the skull. Grounding electrodes 320 may include or be at least one ring electrode (e.g., FIGS. 5, 6, 10, and 11).

Figure 7:
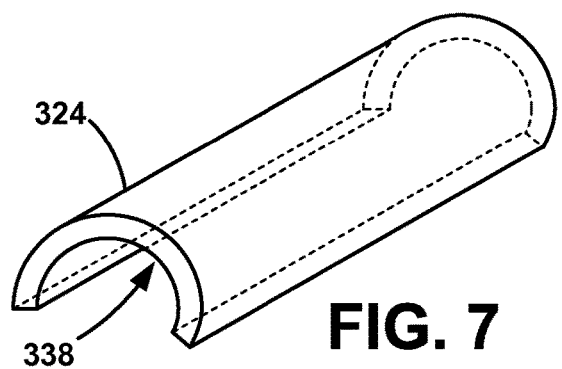
FIG. 7 is a conceptual drawing of an example grounding electrode that is a ring segment electrode defining a circumferential arc.

In some examples, grounding electrodes 320 may include or be at least one ring segment electrode (e.g., FIG. 7). In one example, grounding electrode 320 may comprise or may be at least one thin-film carried electrode and/or a coil electrode and/or wire electrode (see e.g., FIG. 8). Grounding electrodes 320 can be formed by a laser cut-out section of insulation covering the electrical conductor of the grounding electrode (e.g., FIG. 9). Grounding electrodes 320 may be at least partially formed by an electrically conductive polymer. In some examples, at least two grounding electrodes may be provided and daisy-chained or otherwise coupled together (e.g., FIGS. 10 and 11). In this manner, the two-daisy chained electrodes may be described together as a single grounding electrode when electrically coupled. In some examples, the grounding electrode 320 may be or may include a wire disposed within an axial lumen having access openings formed in the elongated body of the connecting cable 120 for entry of body fluids (e.g., FIG. 12).

In one example, lead 300 of the system 100 may be at least partially protected and surrounded by a protective tubing element. The grounding electrode may be arranged on top, or external, of the protective tubing element.

DBS system 100, or system 101, can be described by having several functions. For example, electrodes 132 may be used for neurostimulation and/or neurorecording. Control electronics, i.e., circuitry housed within the first module 110 (IPG) and the second module 111 (ALC), are used to provide neurostimulation and/or neurorecording via the plurality of electrodes 132. It is possible that only one of the electrodes 132, but also more or all of the electrodes 132, are used to provide an electrical stimulation field. The grounding electrode 320 is configured to establish a defined return path for the stimulation current from electrodes 132, which is used to provide the electrical stimulation field.

By arranging at least one grounding electrode 320 in the vicinity of the control electronics, e.g., the first module 110 and/or the second module 111, the noise on the recording signal that could be caused for instance by residual signal(s) through ohmic lines to the control electronics may be reduced as compared to other locations for a grounding electrode. In contrast, a grounding electrode located in the vicinity of the electrodes 132, which are used for neurostimulation and neurorecording, may cause undesirable noise or disturbances of the stimulation signal or the recording signal. Therefore, an arrangement of the grounding electrode 320 next to or adjacent of the control electronics may be advantageous.

Such an arrangement of the grounding electrode 320 on connecting cable 120 next to the control electronics, e.g., next to first module 110 or second module 111, is especially configured such that the grounding electrode 320 reduces any risk of tissue encapsulation due to an electrode causing defects at the electronics package (e.g., the first or second module housing control circuitry).

A defined return path may be for example a uni-lateral return path (e.g., on the same side of the brain that the corresponding electrodes are implanted) that has a focused, or non-dissipated return path for the stimulation current, due to the location and/or size of the return electrode 320. Grounding electrode 320 may be configured of a shape and/or size that provides a more defined or focused return path than a larger structure such as the entire housing of IPG 110, for example. However, if a more dispersed or less defined return path is desired, electrode 320 may be configured with a larger surface area as described herein in other examples. Also, in case of bilateral stimulation, a grounding electrode near the control electronics (e.g., ground electrodes 320 positioned adjacent to respective modules 111) may help to ensure that the return path(s) stay unilateral. For example, current from electrodes 132A may return to return electrode 320A while current from electrodes 132B may return to return electrode 320B (e.g., the electrical current remains on its respective hemisphere of the brain.

In some examples, a system (e.g., system 100 or 101) for neurostimulation and/or neurorecording includes a plurality of electrodes for neurostimulation and/or neurorecording, control electronics for providing neurostimulation and neurorecording via at least one of the plurality of electrodes, and at least one grounding electrode being arranged in the vicinity of the control electronics. The grounding electrode may be configured to establish a defined return path for the stimulation current delivered by one of the plurality of electrodes on a lead. The grounding electrode may be electrically coupled to a ground signal of first module 110 and/or second module 111.

In some examples, arranging at least one grounding electrode in the vicinity of the control electronics (e.g., near second module 111) may reduce the noise on the recording signal that would otherwise be caused by residual signal(s) through ohmic lines to the control electronics. Conversely, a grounding electrode in the vicinity of the plurality of electrodes used for neurostimulation and/or neurorecording might cause undesirable noise or disturbances of the stimulation signal or the intrinsic signals being recorded.

Therefore, in some examples, an arrangement of the grounding electrode next to the control electronics (e.g., within second module 111) may be advantageous. For example, as discussed above, disposing the grounding electrode next to the control electronics (e.g., of second module 111) instead of with the control electronics (e.g., on a housing of second modules 111) may reduce the risk that the grounding electrode causes encapsulation defects to the housing at the electronics package (e.g., second module 111). In some examples, employing example systems for neurostimulation and/or neurorecording according to the present disclosure may avoid a short circuit effect that can result from inadequate encapsulation of the electronics. Such inadequate encapsulation, or breaches of the housing or casing of the electronics, can occur due to breaches in the encapsulation layer such as a hole in the encapsulation or casing that may occur due to return current residing at the housing of the module. Any faults in the encapsulation, or housing, of the module may be highly likely to cause short circuit problems within the control electronics of the module. In other words, the casing of second module 111 may be compromised if a return electrode is disposed on the casing of the second module. By placing one or more return electrodes proximal of second module 111, for example, second module 111 may be adequately encapsulated which may reduce the encapsulation related problems.

A defined return path provided by the grounding electrode may be, for example, a uni-lateral return path and/or a focused, non-dissipated return path for the stimulation current delivered by other electrodes. Also, in case of bilateral stimulation (e.g., stimulation of the brain provided by leads on respective sides of the brain (e.g., system 101), a grounding electrode near the control electronics (e.g., modules 111) may ensure that the return path(s) stay(s) unilateral (e.g., the stimulation delivered to one hemisphere of the brain does not return via a return path in the other hemisphere of the brain).

In some examples, control electronics of the system may be arranged in at least two modules (e.g., first module 110 and second module 111). A modular approach with the control electronics being arranged in at least two modules may allow for a minimally invasive implantation, which may be beneficial for the patient. For example, the first module 110 may be an implantable pulse generator and the second module 111 may be an active lead can that includes a switch matrix. First module 110 may include other circuitry such as a power supply (e.g., battery), one or more processors, one or more memories, communication units, sensors, or any other components. Second module 111 may include the switch matrix and a processor that controls the switch matrix. In some examples, second module 111 may include one or more pulse generators in addition to, or instead of, those provided by module 110.

The grounding electrode may be arranged between the first module 110 (e.g., an implantable pulse generator) and the second module 111 (e.g., active lead can), e.g., proximal of the second module 111. The grounding electrode 320 may be easily placed on and/or integrated into a connecting cable 120 between the implantable pulse generator and the active lead can. In some examples, the grounding electrode may be arranged distal of the active lead can. With this approach, the return path of the stimulation current from the stimulation electrode to the grounding electrode may stay well-defined, as the path may be sufficiently long while preventing increased resistance and noise that would occur with a return electrode on first module 110.

The grounding electrode 320 may be in the vicinity of the second module 111 (i.e., the active lead can (ALC)). The active lead can may be connected and/or mounted to a lead 300 carrying the electrodes for neurostimulation and/or neurorecording. Therefore, it may be advantageous for the grounding electrode to be arranged in the vicinity of the active lead can (second module 111). In this manner, the grounding electrode may be configured to be implanted with the system such that the grounding electrode is only partially covered by tissue or fully uncovered by the tissue to be stimulated. This well-defined current path from the stimulation site of the electrodes to the grounding electrode and out of the tissue may be provided. For example, the tissue may be at least partially brain tissue. Also, the grounding electrode may be at least partially placed in the vicinity of the second module 111 and/or at least partially outside of the skull.

The size of the grounding electrodes 320A and 320B (or a single ground electrode for a single second module 111) may be selected based on the sizes of the electrodes 132A or 132B of the respective lead 300A or 300B. For example, the surface area of the grounding electrode 320 may be greater than a total surface area of all of the plurality of electrodes on the respective lead. In this example, the surface area of grounding electrode 320A may have a greater surface area than the total surface area of all of electrodes 132A. In one example, the total surface area of electrodes 132A may be approximately 16 mm$^2$ and the surface area of grounding electrode 320A may be approximately 20 mm$^2$. In other examples, the size of the grounding electrode may be as large as possible without limiting flexibility of connecting cable 120 or the placement of system 100 within a patient. Larger surface areas of grounding electrodes may reduce the concentration of electrical current.

In addition, grounding electrodes may have edges of various shapes. A grounding electrode may have edges having 90 degree angles in some examples or even more acute angles to facilitate construction of system 100. In other example, the edges of grounding electrodes may have a greater than 90 degree angle, or rounded edges. These more obtuse edges may reduce charge buildup during stimulation and/or during magnetic resonance imaging (MRI) procedures.

Figure 5:
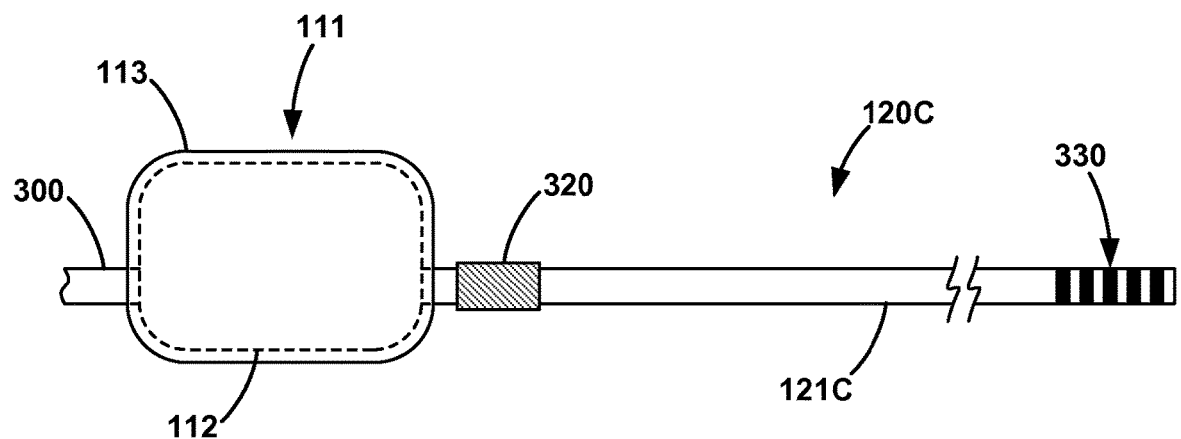
FIG. 5 is a schematic drawing of an example grounding electrode disposed on a connecting cable between a first module and a second module.

FIG. 5 is a schematic drawing of an example grounding electrode 320 disposed on a connecting cable 120C between a first module 110 and a second module 111. Second module 111 is coupled to a lead 300 carrying a plurality of electrodes and connecting cable 120C (e.g., similar to connecting cable 120 described above). Connecting cable 120C includes an elongated body 121C covering electrical conductors (not shown) connecting electronics 112 of second module 111 to electrical contacts 330. Contacts 330 may be configured to couple to first module 110 or another cable. Electronics 112, such as a switch matrix, may be encapsulated or housed by a casing 113.

As shown in FIG. 5, grounding electrode 320 may be a ring electrode placed proximal of the second module 111 on connecting cable 120C. In some examples, grounding electrode 320 may be raised from the surface of elongated body 121C. In other examples, grounding electrode 320 may be recessed into elongated body 121C such that the diameter of grounding electrode 320 is approximately equal to the diameter of elongated body 121C. Alternatively, the grounding electrode 320 can be directly placed on the elongated body 121C of the connecting cable 120C.

The grounding electrode 320 may include or may be at least one ring electrode or ring segment electrode. A ring segment electrode may have a partial circumference such as an arc less than 360 degrees and greater than 180 degrees. Ring electrodes may provide a very effective grounding effect for stimulation signals.

In some examples, grounding electrode 320 may be at least partially formed and/or covered by an electrically conductive or noninsulative polymer. The electrically conductive polymer may be a biocompatible polymer. Furthermore, the noninsulative polymer may be expanded polytetrafluoroethylene (ePTFE) or a similar material. Such a polymer may prevent tissue ingrowth or inflammation reactions with grounding electrode 320 and ensures that the ground electrode 320 site remains electrically active. The material ePTFE is not electrically conductive. Although ePTFE is not itself conductive, it may be non-insulative in a soaked ionized environment within the body. Ions, and therefore electricity, are able to pass through the material. Coating the grounding electrode may allow the size of the grounding electrode to be adjusted, such as being reduced in size. These features may be applied to any of the grounding electrodes described herein.

Figure 6:
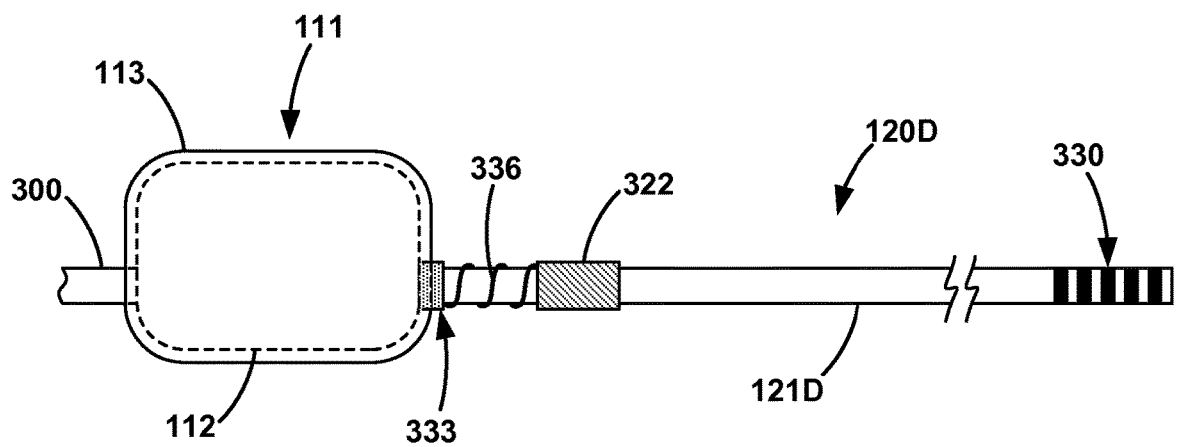
FIG. 6 is a schematic drawing of an example grounding electrode coupled to a second module via a coiled conductor and a contact pad of the second module.

FIG. 6 is a schematic drawing of an example grounding electrode 322 coupled to a second module 111 via a coiled conductor 336 and a contact pad 333 of the second module 111. Second module 111 is coupled to a lead 300 carrying a plurality of electrodes (not shown in FIG. 6) and connecting cable 120D (e.g., similar to connecting cable 120 described above). Connecting cable 120D includes an elongated body 121D covering electrical conductors (not shown) connecting electronics 112 of second module 111 to electrical contacts 330.

As shown in FIG. 6, grounding electrode 322 (e.g., a ring or ring segment electrode) may be coupled to coil electrode 336 and may be placed on elongated body 121D of connecting cable 120D near the second module 111. Coil electrode 336 may be connected to a ground terminal, or contact pad 333, of second module 111 (either alone or via an intermediate component, or via an internal wire within connecting cable 120D). Grounding electrode 322 and/or coil electrode 336 may be disposed over elongated body 121D and/or disposed flush with the external surface of elongated body 121D.

In some examples, an encapsulant (e.g., an adhesive) may interface with the surface of the grounding electrode 322 and/or coil electrode 336 to improve adhesion to elongated body 121D. In some examples, coil electrode 336 may be an insulated coil conductor. In other examples, the grounding electrode 322 and/or coil electrode 336 may have a coating of ePTFE or other similar material. Such a coating may be a coating that enhances electrical characteristics of grounding electrode 322. This coating may be applied to any metallic surface. Also, ePTFE or similar material around an externalized coil/laser cut tube/series of conductors may be provided to prevent tissue ingrowth and/or ensure that the electrode area remains electrically active. In other examples, grounding electrode 322 and/or coil electrode 336 may include coatings such as iridium-oxide material (IROX), sputtered platinum, titanium nitride, etc. These materials may enhance the electrical characteristics of an electrode.

Alternatively or additionally, when ring grounding electrode 322 is placed on the connecting cable 120D adjacent to second module 111, as shown in FIG. 6, a coiled metal conductor 336 may be used between the grounding electrode 322 and the second module 111. The casing 113 of second module 111 could display a metallic neck (e.g., contact pad 333) for establishing a contact for coiled electrode 336 or a coiled conductor. Contact pad 333 may be formed or attached to second module 111 and/or coiled electrode 336 by laser welding or other suitable manufacturing methods.

FIG. 7 is a conceptual drawing of an example grounding electrode 324 that is in the form of a ring segment electrode defining a circumferential arc 338. The ring segment electrode 324 may be used for other grounding electrodes described herein. In this manner, a grounding electrode (e.g., grounding electrode 320) may include at least one ring segment. Such a grounding electrode 324 can cover or form a circumferential arc 338 having more than 180 degrees.

A typical full ring electrode may have a circumferential arc that encompasses 360 degrees because the arc is a full circle. In contrast, the ring segment electrode 338 may define a circumferential arc greater than 180 degrees and less than 360 degrees. The ring segment of grounding electrode 324 may be disposed on connecting cable 120, or any other structure, in a circumferential orientation selected such that the circumferential arc 338 is directed toward the location at which the plurality electrode 132 of lead 300 will be located. In other words, grounding electrode 324 may be positioned with circumferential arc 338 facing towards the skull in examples where the ring segment electrode is implanted on the skull and beneath the skin. Other orientations may also be used.

Figure 8:
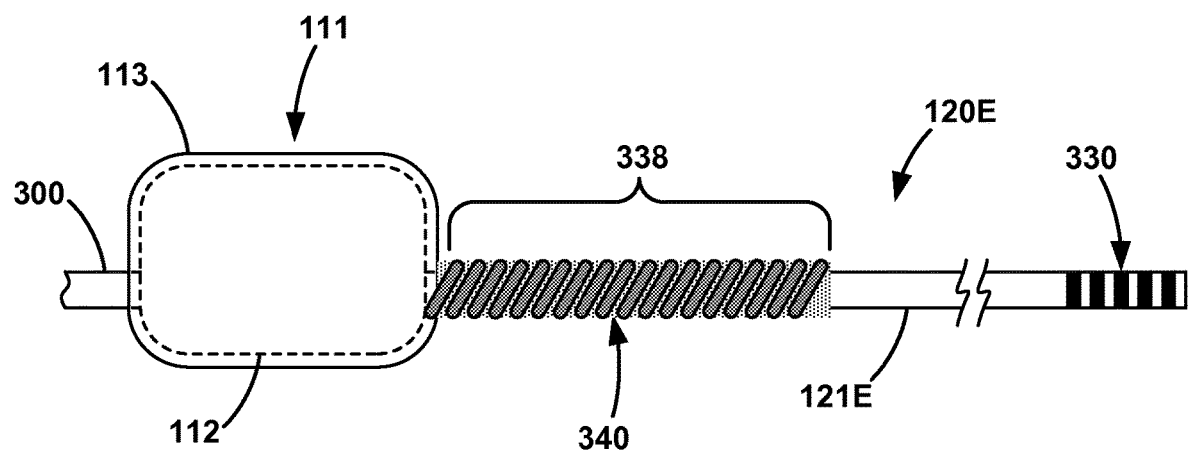
FIG. 8 is a schematic drawing of an example grounding electrode comprising a coiled conductor.

FIG. 8 is a schematic drawing of an example grounding electrode 338 comprising a coiled conductor. The coiled conductor of grounding electrode 338 may be used as, or as part of, any grounding electrodes described herein. As shown in FIG. 8, a bare coil conductor (or coil electrode) is used to form a grounding electrode 338. The coiled configuration of the conductor is flexible and can provide increased flexibility to connecting cable 120E and elongated body 121E as compared to having a solid ring electrode over elongated body 121E. The coiled conductor may be electrically coupled to electronics 112 within second module 111. In some examples, a portion of casing 113 covering electronics 112 may also cover at least a portion of the coil conductor of grounding electrode 338.

Grounding electrode 338 may be formed by coiling a conductor wire, or assembling a pre-coiled conductor, around the exterior surface of elongated body 121E. In other examples, grounding electrode 338 may be at least partially formed by at least one of a laser cut-out, a laser pattern, or laser-ablation. In this manner, a solid or semi-solid electrode may have portions of it removed to create a coiled conductor. In other examples, portions of the electrode may be removed along the length of the structure to create a flexible structure, such as semi-circular arches running lengthwise along the electrode. The flexible structure may then be capable of flexing like a coil without being a coiled conductor.

In some examples, the coil conductor may remain exposed. In other examples, an adhesive 340 may be used to backfill the coil conductor of grounding electrode 338 in order to prevent tissue ingrowth between each turn of the coil. The adhesive, or other material, may form a smooth covering over the coil. In other examples, ePTFE may cover at least a portion of the coil conductor to reduce or avoid tissue ingrowth.

In one example, grounding electrode 338 may include, or be constructed of, a thin-film carried electrode, a coil electrode, and/or a wire electrode. If the structure carrying the electrodes is a lead or cable that includes thin film structures, grounding electrode 338 may be constructed by arranging the ground electrode into the thin film structure. Coils or wires may alternatively be used to manufacture and provide the grounding effect for stimulation signals delivered by other electrodes.

Figure 9:
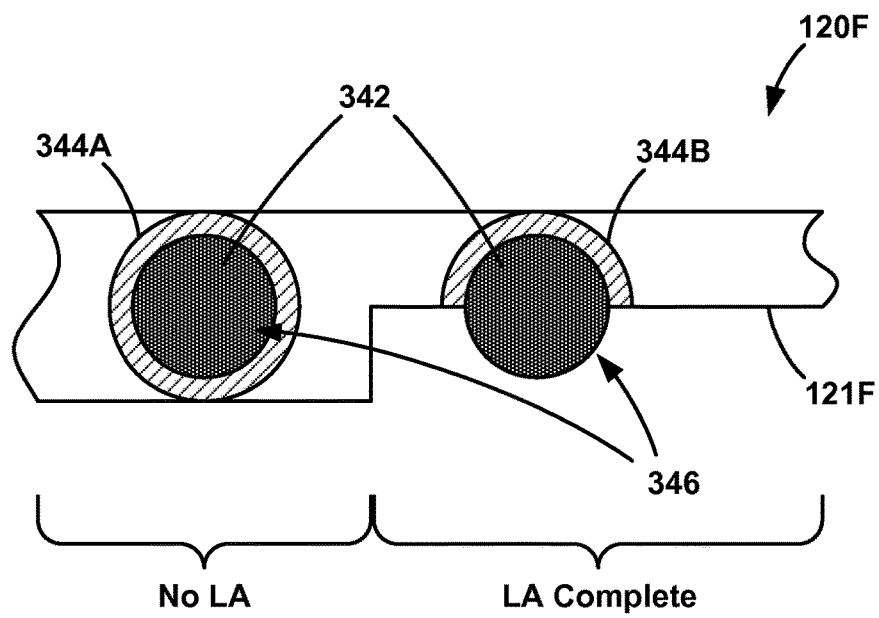
FIG. 9 is a schematic drawing of an example grounding electrode formed from ablation of material covering at least a portion of the grounding electrode.

FIG. 9 is a schematic drawing of an example grounding electrode formed from ablation of material covering at least a portion of the grounding electrode 346. As shown in FIG. 9, grounding electrode 346 may include conductor 342. Conductor 342 may be a coiled conductor (of which only a portion is shown in FIG. 9) that is insulated with outside coating 344 (which includes coating portions 344A and 344B). In addition, conductor 342 and coating 344 may be encased in the material forming elongated body 121F of connecting cable 120F. Conductor 342 may be coupled to second module 111.

To form ablation electrode 346 and expose conductor 342, laser ablation may be performed to ablate and remove at least part of outside coating portion 344B. "No LA" portion of connecting cable 120F refers to the structures when no laser ablation has occurred. In this form, conductor 342 is insulated by elongated body 121F and coating portion 344A. "LA Complete" refers to the portion of connecting cable 120F in which part of elongated body 121F and coating portion 344B has been laser ablated to remove the insulating material and expose conductor 342 for use as a grounding electrode. Although laser ablation may be used, other processing methods, such as heat ablation or mechanical removal may be employed to remove the portions of coating 344 and elongated body 121F.

Figure 10:
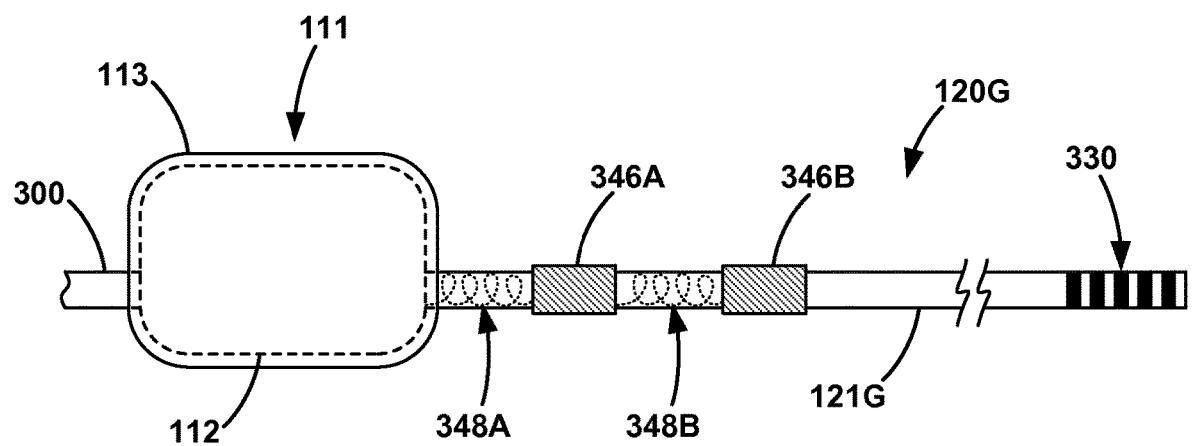
FIG. 10 is a schematic drawing of example grounding electrodes daisy-chained together.

Any grounding electrode described herein may be at least partially formed by a laser cut-out section and/or by laser-patterning and/or by laser-ablation. With a laser cut-out, conductive sections of an already existing system ground line may be laid open to form a grounding electrode. Very accurate and small grounding electrodes may be constructed using this method. In other words, laser energy may be used to remove insulating material over a conductor and/or remove portions of the conductor itself. By laser-ablation and/or laser-patterning, the flexibility of the grounding electrode may be adjusted, modified, and increased in some examples. In this manner, electrode 346 could include one continuous cut-out section or multiple discontinuous cut-out sections. FIG. 10 is a schematic drawing of example ring electrodes 346A and 346B daisy-chained together to form multiple grounding electrodes. In order to increase the surface area of a grounding electrode (if necessary), multiple ring electrodes 346A and 346B (collectively "grounding electrodes 346") can be daisy-chained, or coupled, using internal or external joints (e.g., conductors internal to elongated body 121G that carries grounding electrodes 346) to from one or more grounding electrodes. Coupled ring electrodes 346 can improve the flexibility of connecting cable 120G by splitting up a single grounding electrode into multiple grounding electrodes disposed on elongated body 121G, permitting the cable to be more flexible between the grounding electrodes. In the example of FIG. 10, internal conductive coils 348A and 348B are used to join the ring electrodes 346 and connect the ring electrodes 346 to electronics 112 of second module 111.

In some examples, the configuration of FIG. 10 may be an example of a first grounding electrode daisy-chained to a second grounding electrode. However, two or more ring electrodes daisy-chained together such that all electrodes electrically coupled may be referred to as a single grounding electrode instead of multiple grounding electrodes. Although conductive coils 348A and 348B are shown as coils, the conductors between ring electrodes 346 and/or ring electrode 346A and electronics 112 may be straight or take the form of different shapes.

At least two grounding electrodes (e.g., ring electrodes or electrodes of any shape) may be provided and daisy-chained together. In some examples, three or more electrodes may all be daisy-chained together. In this manner, the grounding effect of the grounding electrode may be enhanced such that undesirable peaks of the returning stimulation current can be reduced or even avoided. Furthermore, daisy-chaining multiple discrete electrodes together, or breaking the ground electrodes up into smaller pieces, may improve the flexibility of the assembly carried by elongated body 121G, and connecting cable 120G, and reduce the length of stiff or rigid regions of connecting cable 120G. In other words, the addition of ring electrodes removes flexibility from connecting cable 120G. However, splitting the surface area of a ring electrode into multiple electrodes coupled together may retain at least some of the flexibility of elongated body 121G at the respective locations without losing electrode surface area providing appropriate grounding of stimulation current.

Figure 11:
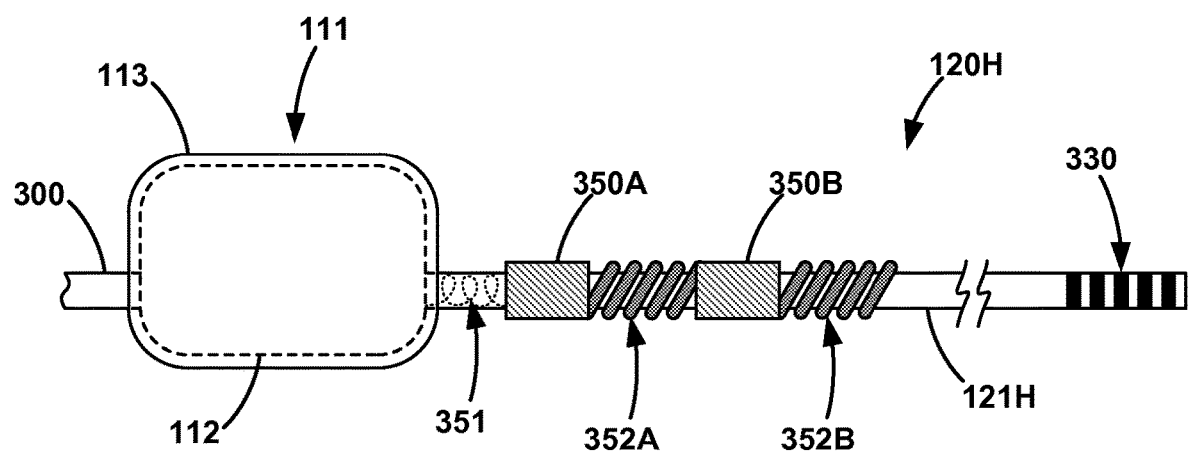
FIG. 11 is a schematic drawing of example grounding electrodes coupled to coiled conductors.

FIG. 11 is a schematic drawing of an example grounding electrode formed by connecting electrodes to coiled conductors. FIG. 11 may be similar to FIG. 10 in that a grounding electrode may be formed by multiple components. As shown in FIG. 11, two ring electrodes 350A and 350B are electrically connected with external coil wire 352A and 352B (e.g., coiled conductors) to form a grounding electrode (e.g., grounding electrode 320). Coil wire 352A and 352B may be external to elongated body 121H of connecting cable 120H and exposed. In this manner, the grounding electrode may be formed by active components of ring electrodes 350A and 350B and coil wire 352A and 352B. In some examples, this configuration may be referred to as daisy-chaining electrodes 350. Ring electrode 350A may be coupled to a contact pad or neck (not shown) of second module 111.

In some examples, coil wire 352A and 352B may be wire conductors that are coiled and coupled (e.g., via welding, soldering, crimping, or conductive adhesive) to adjacent ring electrodes. In other examples, ring electrodes 350A and 350B (or a single ring electrode) may be a laser-cut tube with the cut-out pattern forming a flexible structure (e.g., coil wire 352A and 352B) that allows the grounding electrode to be flexible for connecting cable 120H. The neck 351 extending proximally onto the connecting cable 120H could be a laser-cut extension of the cable mounting means, in some examples.

Figure 12:
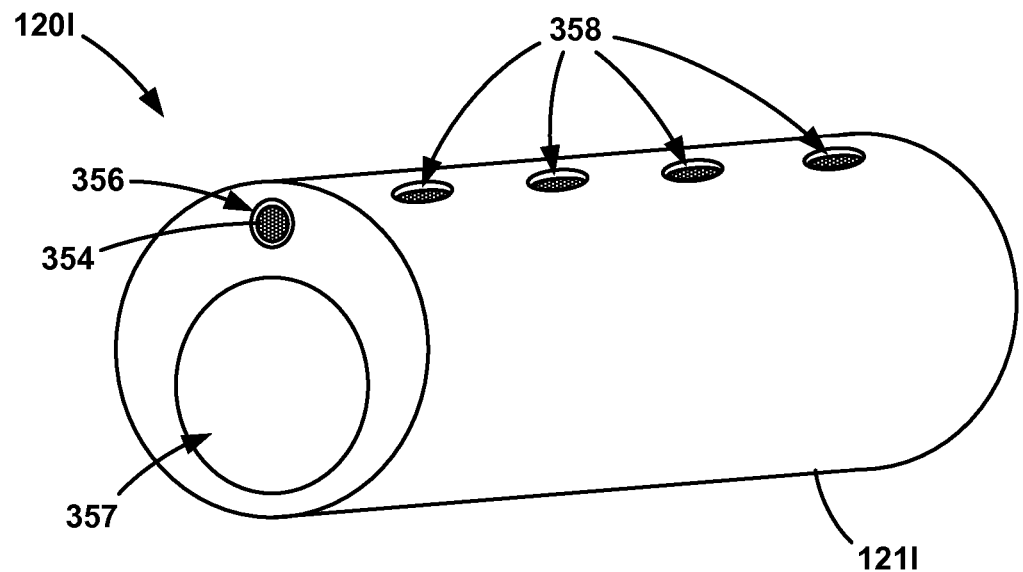
FIG. 12 is a schematic drawing of an example ground electrode disposed within an axial lumen having access openings.

FIG. 12 is a schematic drawing of an example ground electrode (e.g., grounding electrode 320) formed from a wire 354 disposed within an axial lumen 356 having access openings 358. Access openings 358 are configured to allow body fluids to contact wire 354. Axial lumen 356 may be defined by elongated body 121I (e.g., an insulator material such as a non-conductive polymer) of connecting cable 120I. Access openings 358 may be formed by molding, mechanical removal, or by laser patterned holes. Conducting wire 354 may be positioned inside axial lumen 356 such that access openings 358, also defined by elongated body 121I, provide a passage for fluid and/or tissue to access lumen 356 from the exterior of elongated body 121I. In this manner, stimulation signals may enter access openings 358 to contact wire 354 and form the grounding electrode.

In this manner, connecting cable 120I may define axial lumen 356 and access openings 358 between the axial lumen 356 and an exterior of connecting cable 120I for entry of body fluids. The grounding electrode may be formed from an electrically conductive wire 354, or other conductive material in any shape, disposed within axial lumen 356. Lumen 357 may be defined by elongated body 121I and be configured to carry one or more conductors that carry communication signals, power signals, stimulation signals, or any other signal between different modules of the system.

A grounding electrode provided according to FIG. 12 may provide effective grounding of stimulation signals since wire 354 is arranged in axial lumen 356 running along a longitudinal length of connecting cable 120I. Therefore, wire 354 may be disposed within axial lumen 356 and one or more conductors that carry respective signals between modules 111 and 110 may be disposed within lumen 357. In addition, elongated body 121I may provide protection for the grounding electrode. Such a grounding electrode assembly may allow for simple construction and manufacturability, and the symmetry of connecting cable 120I may be improved to provide a cosmetically pleasing device.

Figure 13:
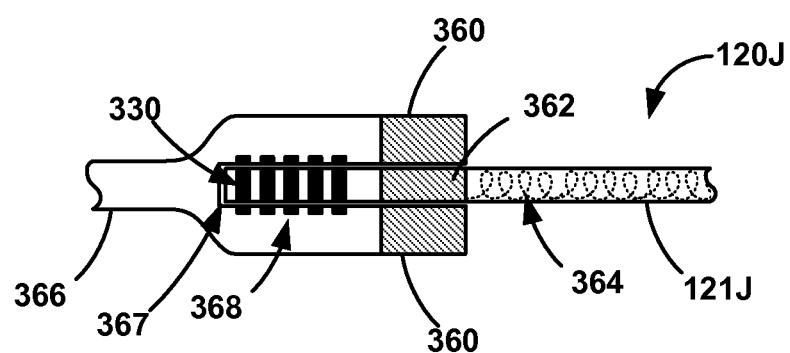
FIG. 13 is a cross-sectional view of an example ground electrode disposed on a distal end of an extension connecting cable configured to couple to a lead connecting cable.

FIG. 13 is a cross-sectional view of an example ground electrode formed by a ring 360 disposed on a distal end of an extension connecting cable 366 configured to couple to a lead connecting cable 120J. In some examples, first module 110 may be coupled to second module 111 by two or more distinct cables that couple together. For example, two cables may combine to electrically couple first module 110 to second module 111. As shown in FIG. 13, an extension connecting cable 366 is configured to couple with lead connecting cable 120J. To establish a grounding electrode (e.g., similar to grounding electrode 320), a ring 360 is added to the distal end of extension connecting cable 366. A proximal end of extension connecting cable 366 may be configured to connect to first module 110 (i.e., to the left of FIG. 13, another module, or another cable, while lead connecting cable 120J may extend in the opposite direction to second module 111 (i.e., to the right of FIG. 13).

The distal end of extension connecting cable 366 may include ring 360 having at least one exposed surface to act as a grounding electrode. Ring 360 may have an exposed surface on the distal surface of the connecting cable 366 and/or an exposed surface on a circumferential surface of extension connecting cable 366 at the distal end. Extension connecting cable 366 may also define a receptacle 367 configured to accept a proximal end of connecting cable 120J. The receptacle may include one or more contacts 368 configured to electrical couple with electrical contacts 330 of connecting cable 120J. Each of contacts 368 may be coupled to conductors (not shown) that travel the length of extension connecting cable 366 to the proximal end adjacent second module 111, for example. Ring electrode 360 may also have an inner surface configured to contact ring contact 362 (or a contact of any shape or size) carried by elongated body 121J of connecting cable 120J. Ring contact 362 may be coupled to conductor 364 disposed within elongated body 121J and configured to carry the return signal back to second module 111. Generally, return current received by ring electrode 360 would return to second module 111 and then possibly back to first module 110 via a conductor coupling first module 110 and second module 111. Alternatively, ring electrode 360 may be directly coupled to a conductor that returns current directly back to first module 110 without first traveling to second module 111.

In one example, extension connecting cable 366 is disposed distal of first module 110 and proximal to lead connecting cable 120J. Extension connecting cable 366 may plug into first module 110, and lead connecting cable 120J may plug into second module 111. Extension connecting cable 366 includes a receptacle 367 that receives connectors or contacts 330 of the lead connecting cable 120J. In addition, extension connecting cable 366 may include at least one ring electrode 360 at a distal end of extension connecting cable 366. The at least one ring electrode 360 is configured to define a grounding electrode and electrically couple to a contact 362 of the lead connecting cable 120J. In this manner, the grounding electrode may be part of a connector of system 100. For example, the ground electrode may be part of the connector of the extension connecting cable, where one or more connecting sections or rings must be added that exit from the extension connecting cable. In some examples, an extra-large ground electrode may be included in the extension connecting cable cavity may be applied externally to the cable such that the return electrode is carried on an external surface of extension connecting cable 366.

In some examples, a grounding electrode may be disposed distal of second module 111 and proximal of other electrodes on a lead. For example, a lead (e.g., lead 300) may be at least partially protected by a protective tubing element over an external surface of the lead body (e.g., a lead body formed by a thin film). The grounding electrode (e.g., grounding electrode 320) may be arranged on top of the protective tubing element. A protective tubing element may improve the stability or robustness of the lead and may form the outermost part of the lead. Thus, placing the ground electrode on the outer surface of the protective tubing element may increase the stability of both the lead and the ground electrode, thus providing an advantageous combination of improved structure of the lead and function of the grounding electrode.

Figure 14:
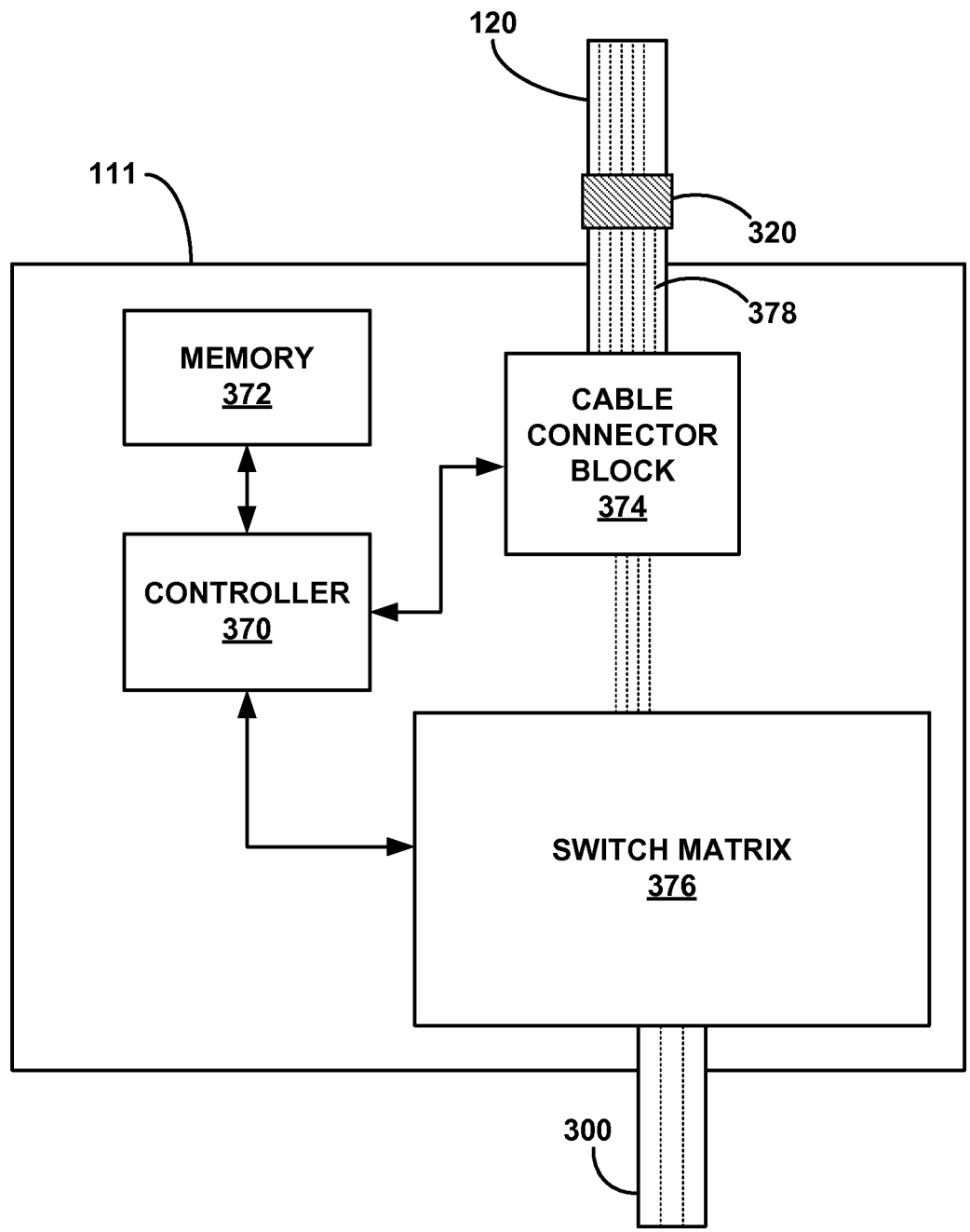
FIG. 14 is a block diagram of an example second module comprising a switch matrix.

FIG. 14 is a block diagram of an example second module 111 comprising a switch matrix 376. Second module 111 may include at least a portion of control electronics of a larger system 100 or 101. As shown in FIG. 14, second module 111 may include controller 370, memory 372, switch matrix 376, and cable connector block 374. In addition, grounding electrode 320 is coupled to second module 111 and switch matrix 376. Second module 111 may include additional components (e.g., one or more pulse generators) in some examples or fewer components in other examples.

In general, second module 111 may comprise any suitable arrangement of hardware, alone or in combination with software and/or firmware, to perform the techniques attributed to second module 111 and system 100 or 101. In various examples, controller 370 may be a processor or include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Memory 372 may be, for example, as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although controller 370 and memory 372 is described as separate modules, in some examples, controller 370 and memory 372 (or more components of second module 111) are functionally integrated.

Controller 370 may receive operating instructions and/or operating power from first module 110 via connecting cable 120. Operating instructions may or may not be stored in memory 372. Controller 370 may selectively close and open switches within switch matrix 376 to couple and decouple electrodes carried by lead 300 to incoming stimulation signals or a ground line carried by connecting cable 120 (which connects to first module 110) or measure voltages between various pairs or groups of electrodes. In addition, controller 370 may selectively connect to grounding electrode 320 using one or more switches of switch matrix 376. Grounding electrode 320 may be coupled to switch matrix 376 via ground line 378 that is connected to cable connector block 374. In some examples, grounding electrode 320 may be coupled to switch matrix 376 without going through cable connector block 374. In some examples, controller 370 may use a distinct mechanism from switch matrix 376 to selectively couple to grounding electrode 320. In this manner, controller 370 may select various electrode configurations (e.g., different sets of at least one anode and at least one cathode) selected from grounding electrode 320 and the plurality of electrodes carried by lead 300. Controller 370 may use different electrode combinations to deliver neurostimulation therapy and/or provide neurorecording functions to system 100.

In one example, system 100 or 101 may be used to provide neurostimulation. The method of delivering neurostimulation may include generating, by a pulse generator of a first module 110, a stimulation signal, transmitting, by connecting cable 120 that connects the first module 110 to a second module 111 including a switch matrix 376, the stimulation signal to at least one electrode of a plurality of electrodes 132 via switch matrix 376. The plurality of electrodes 132 may be disposed distal of second module 111, such as on lead 300 coupled to second module 111. In addition, the method may include returning the stimulation signal to first module 110 via grounding electrode 320 disposed distal of first module 110 and proximal of second module 111. In one example, grounding electrode 320 may be carried by connecting cable 120 coupling first module 110 and second module 111.

In another example, system 100 or 101 may be configured to provide neurorecording functions. System 100 or 101, which may or may not include a pulse generator, may measure a brain signal between at least one electrode of a plurality of electrodes 132 and grounding electrode 320. The grounding electrode 320 may be disposed distal of first module 110 including a pulse generator and proximal of second module 111 including a switch matrix 376. First module 110 and second module 111 may be connected by a connecting cable 120, and electrodes 132 may be disposed distal of second module 111.

While techniques described herein are discussed primarily in regards to DBS therapy, one or more such techniques may be applied to treat disorders such as chronic pain disorders, urinary or fecal incontinence, sexual dysfunction, obesity, gastroparesis, and may involve other types of stimulation such as spinal cord stimulation, cardiac stimulation, pelvic floor stimulation, sacral nerve stimulation, peripheral nerve stimulation, peripheral nerve field stimulation, gastric stimulation, or any other electrical stimulation therapy.

In addition, it should be noted that system 100 or 101 may not be limited to treatment or monitoring of a human patient. In alternative examples, system 100 or 101 may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules (e.g., modules 110 and 111) and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A system for neurostimulation, the system comprising:
   a first module comprising a pulse generator within a first housing;
   a second module comprising a switch matrix within a second housing distinct from the first housing;
   a connecting cable that connects the first module to the second module;
   a grounding electrode disposed distal of the first module and proximal of the second module, wherein the grounding electrode is electrically coupled to the switch matrix of the second module; and
   a plurality of electrodes disposed distal of the second module, wherein each electrode of the plurality of electrodes are selectively coupled to the pulse generator via the switch matrix.

2. The system of claim 1, wherein the grounding electrode is configured to establish a defined return path for stimulation current delivered by the pulse generator to one or more electrodes of the plurality of electrodes.

3. The system of claim 1, further comprising control electronics for the plurality of electrodes and the grounding electrode, the control electronics configured to at least one of provide neurostimulation current or sense neuro signals via at least one electrode of the plurality of electrodes and the grounding electrode, wherein the control electronics are arranged in at least one of the first module or the second module.

4. The system of claim 1, wherein the grounding electrode is disposed closer to the second module than the first module.

5. The system of claim 1, wherein the grounding electrode is configured to be implanted at least partially outside of a skull of a patient, and wherein the plurality of electrodes are configured to be implanted at least partially within brain tissue.

6. The system of claim 1, wherein the grounding electrode is carried by the connecting cable.

7. The system of claim 1, wherein the switch matrix is configured to select an electrode configuration from the plurality of electrodes and the grounding electrode for delivery of electrical stimulation pulses from the pulse generator.

8. The system of claim 1, wherein the grounding electrode comprises at least one ring electrode.

9. The system of claim 1, wherein the grounding electrode comprises at least one ring segment electrode, the ring segment electrode defining a circumferential arc greater than 180 degrees and less than 360 degrees.

10. The system of claim 1, wherein the grounding electrode comprises a coil electrode.

11. The system of claim 1, wherein the grounding electrode is at least partially formed by at least one of a laser cut-out, a laser pattern, or laser-ablation.

12. The system of claim 1, wherein the grounding electrode is at least partially covered by at least one of an electrically conductive polymer or a noninsulative polymer.

13. The system of claim 1, wherein the grounding electrode is a first grounding electrode, and wherein the system comprises a second grounding electrode coupled to the first grounding electrode via one or more conductors internal of the connecting cable.

14. The system of claim 1, wherein the grounding electrode is a first grounding electrode, and wherein the system comprises a second grounding electrode, and wherein the first and second grounding electrodes are ring electrodes coupled by a coiled conductor disposed external of the connecting cable.

15. The system of claim 1, wherein the connecting cable defines an axial lumen and access openings between the axial lumen and an exterior of the connecting cable for entry of body fluids, and wherein the grounding electrode comprises an electrically conductive wire disposed within the axial lumen.

16. The system of claim 1, wherein the connecting cable is a first connecting cable, and wherein the system further comprises a second connecting cable disposed distal of the first module and proximal to the first connecting cable, the second connecting cable comprising:
   a receptacle that receives connectors of the first connecting cable; and
   at least one ring electrode at a distal end of the second connecting cable, the at least one ring electrode configured to define the grounding electrode and electrically couple to a contact of the first connecting cable.

17. The system of claim 1, wherein a surface area of the grounding electrode is greater than a combined surface area of the plurality of electrodes.

18. The system of claim 1, further comprising a lead electrically coupled to the switch matrix of the second module, wherein the lead comprises a thin film carrying the plurality of the electrodes.

19. A method for neurostimulation, the method comprising:
   generating, by a pulse generator within a first housing of a first module, a stimulation signal;
   transmitting, by a connecting cable that connects the first module to a second module comprising a switch matrix within a second housing distinct from the first housing, the stimulation signal to at least one electrode of a plurality of electrodes selectively coupled to the pulse generator via the switch matrix, the plurality of electrodes disposed distal of the second module; and
   returning the stimulation signal to the first module via a grounding electrode disposed distal of the first module and proximal of the second module, wherein the grounding electrode is electrically coupled to the switch matrix of the second module.

20. A method for neurorecording, the method comprising:
   measuring a brain signal between at least one electrode of a plurality of electrodes and a grounding electrode, the grounding electrode disposed distal of a first module comprising a pulse generator within a first housing and proximal of a second module comprising a switch matrix within a second housing distinct from the first housing, the first module and second module being connected by a connecting cable, and the plurality of electrodes disposed distal of the second module, wherein each electrode of the plurality of electrodes are selectively coupled to the pulse generator via the switch matrix, and wherein the grounding electrode is electrically coupled to the switch matrix of the second module.

* * * * *